United States Patent [19]

Barberet et al.

[11] Patent Number: Plant 5,511

[45] Date of Patent: Jul. 9, 1985

[54] CARNATION NAMED LONDETON

[75] Inventors: Nicole Barberet; Yves Ducloux, both of Antibes, France

[73] Assignee: Laboratoire de Physiologie Vegetale de la Londe SCS Barberet & Ducloux, La Londe, France

[21] Appl. No.: 516,569

[22] Filed: Jul. 25, 1983

[51] Int. Cl.[3] ..... A01H 5/00

[52] U.S. Cl. ..... Plt./71

[58] Field of Search ..... Plt./70, 71

*Primary Examiner*—Robert E. Bagwill

*Attorney, Agent, or Firm*—Chas. W. Rummler

[57] ABSTRACT

A new spray carnation cultivar particularly distinguished by its profuse production of small light pink flowers of a China Rose and Neyron Rose coloration borne on strong, upright stems. This plant has a vigorous, upright and rather rigid growth habit with abundant foliage and a height averaging about 95 cm. at eight months. In particular, this variety is resistant to *Fusarium oxysporum.*

1 Drawing Figure

BACKGROUND OF THE NEW PLANT

Our new spray carnation cultivar is the result of breeding efforts carried on by us at La Londe, Les Maures, France, since 1978 with the object of developing a spray carnation of nice color and good quality of flower and plant growth and particularly a resistance to *Fusarium oxysporum.* This new plant originated as a seedling produced from our crossing of selected and individually identified plants growing among our stock of spray carnation plants maintained at La Londe for breeding purposes. This particular seedling was selected by us for propagation and test because of its nice flower color, profuse production of blooms and its resistance to *Fusarium oxysporum,* and this discovery plant was reproduced by us at La Londe, by means of cuttings. The result of that propagation effort appearing to be very favorable with respect to retention of the novel characteristics of the parent plant, its propagation was continued under our direction through several successive generations, which established that the novel and distinctive characteristics of the discovery plant were fully retained from generation to generation and appeared to be firmly fixed.

DESCRIPTION OF THE DRAWING

Our new carnation cultivar is illustrated by the accompanying photographic drawing which shows, in full color, a typical spray showing buds and flowers in various stages of opening, the colors shown being as nearly true to those herein specified as is reasonably possible to obtain by conventional photographic procedures.

DESCRIPTION OF THE NEW PLANT

The following is a detailed description of our new spray carnation variety based upon observations of greenhouse grown plants made at La Londe, France, in the Spring of 1983, the color designations being specified according to The R.H.S. Colour Chart published by The Royal Horticultural Society of London, England.

THE PLANT

Origin: Seedling.

Parentage:

*Seed parent.*—Stock Plant No. 73 M P 3.

*Pollen parent.*—Stock Plant No. 415 M P. These unnamed varieties are individually identified in our permanent records and are maintained for breeding purposes in our collection of spray carnation plants at La Londe, France.

Classification:

*Botanic.*—*Dianthus caryophyllus.*

*Commercial.*—Spray Carnation.

Form: Erect bush, having at least four stems emitted near the ground.

Height: Average about 95 cm. at eight months.

Main stem:

*Length.*—Less than 15 cm. due to pinching.

Branching character: Normally branched.

Growth habit: Vigorous, upright and rather rigid.

Foliage:

*Quantity.*—Rather abundant.

*Number of leaves.*—At least 120.

*Size of leaf.*—Averaging about 10 cm. long and 1 cm. wide at the seventh node.

*Shape.*—Linear with curved margins.

*Texture.*—Leathery.

*Color.*—Upper side — 189A. Under side — 189A.

*Ribs and veins.*—Hardly noticeable.

*Rachis.*—Hardly noticeable.

THE BUD

Shape: Long ovoid.

Opening rate: About normal for carnations.

Color of petals:

*When sepals first divide.*—More clear than at full bloom.

*When petals begin to unfurl.*—More clear than at full bloom.

Sepals:

*Number.*—Five (exceptionally six).

*Shape.*—Joined at lower part with generally acute upper ends sharply pointed at the apex. The sepals are hooded over the bud and stand up when the flowers open.

*Color.*—Inside — Greenish white. Outside — 137C and 144B.

*Striae.*—Longitudinal.

Calyx:

*Shape.*—Long and cylindrical.
*Size.*—Medium.
*Splitting.*—The calyx does not split.
*Aspect.*—Smooth.

Flower stem:
*Length.*—About 58 cm.
*Character.*—Erect and rather thin.
*Color.*—189A.

THE FLOWER

Blooming habit: Recurrent and blooming profusely during midseason of Spring and Fall.

Size of bloom: Small.
*Diameter.*—Averages about 5 cm.
*Depth.*—Averages about 4.5 cm.

Borne: In cluster.

Shape:
*When bloom first opens.*—High centered.
*When bloom matures.*—Dome shaped. p0 Petalage:
*Number of petals.*—Average about 31.
*Arrangement.*—Imbricated.
*Form.*—Very rounded fan with a very finely serrated edge.
*Texture.*—Soft.
*Appearance.*—Satiny.
*Color.*—Outer Petal: Body — mainly China Rose 58D with Neyron Rose 55C at outer end portion. Base — Yellowish green. Reverse side — 58D and 55D. Inside Petal: Body — 58D and 55C. Base — Yellowish green. Reverse side — 58D and 55D.

Petaloids:
*Number.*—Less than six.
*Size.*—Smaller than the petals.
*Color.*—Same as the petals.

Flower stem:
*Length.*—About 58 cm. (cut at the tenth node).
*Character.*—Upright and of good strength.
*Color.*—189A.

Fragrance: Fragrance is present.

Persistence: The flowers hang on and dry.

Lasting quality:
*As cut flower.*—At least ten days in vase keeping.

Disease resistance: Resistant to *Fusarium oxysporum* as observed INRA, Antibes, Alpes-Maritimes, France.

REPRODUCTIVE ORGANS

Stamens:
*Number.*—7 To 20.
*Arrangement.*—Around the pistils.
*Anthers.*—Size: Less than 4 mm. Color: Whitish.
*Filaments.*—Color — Whitish.

Pistils:
*Number.*—Two (exceptionally three).
*Styles.*—Color — White.
*Stigmas.*—Color — Very light pinkish white.

Character of ovaries: Lightly ribbed.

This new carnation plant most resembles "Sam's Pride" but differs from "Sam's Pride" by having a smaller flower and a more branched spray. Furthermore, this new variety is resistant to *Fusarium oxysporum.*

We claim:

1. The new variety of spray carnation, substantially as herein shown and described, characterized by the profuse production of its medium sized blooms of a light pink color; by its advantageous growth habit; and by its resistance to *Fusarium oxysporum.*

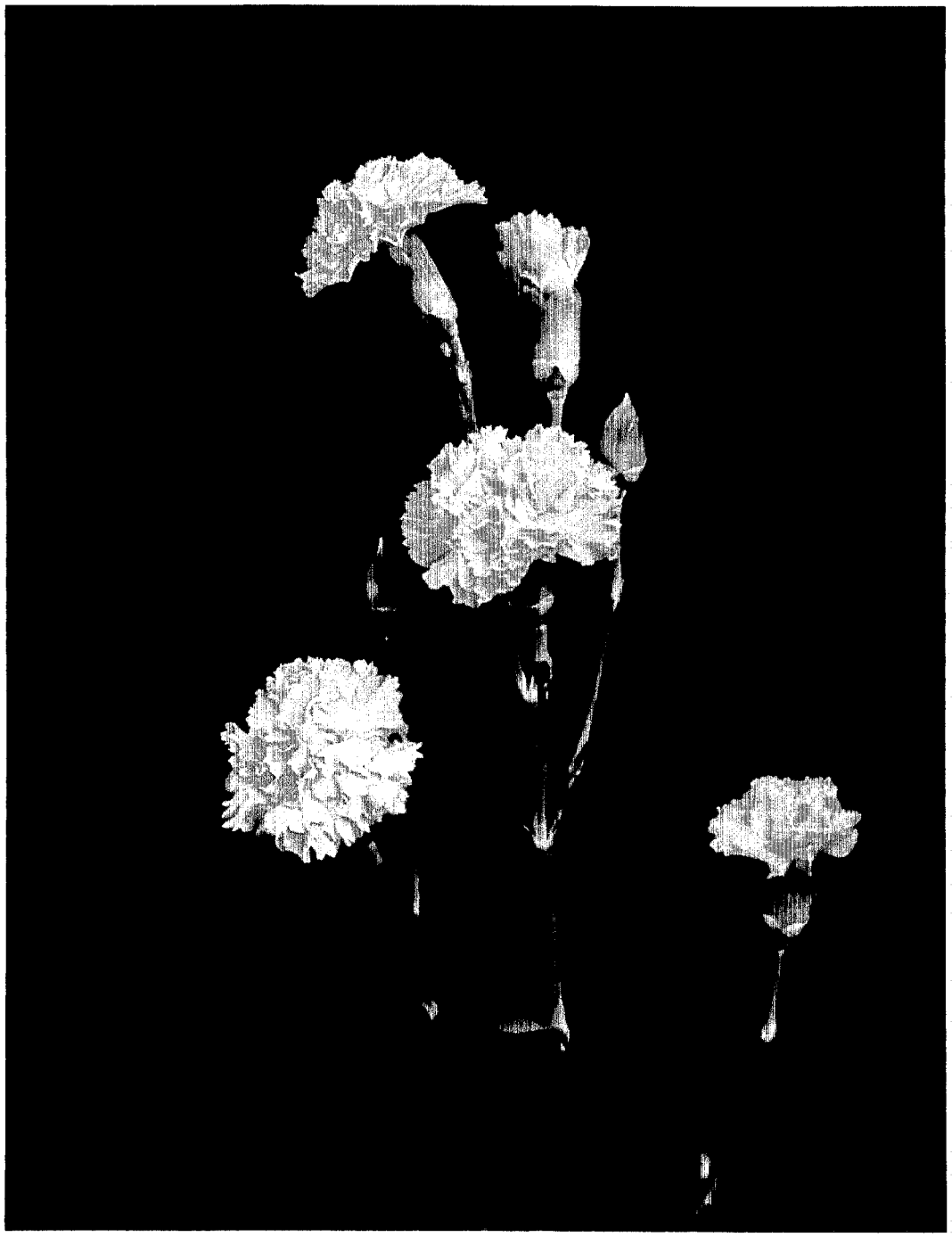

* * * * *